United States Patent [19]
Scholla et al.
[11] Patent Number: 5,059,420
[45] Date of Patent: Oct. 22, 1991

[54] ANTIMICROBIAL STAIN-RESIST CARPET TREATMENT

[75] Inventors: Michael H. Scholla, Wilmington; Yashavant Vinod, Hockessin, both of Del.

[73] Assignee: E. I. duPont de Nemours and Company, Wilmington, Del.

[21] Appl. No.: 509,986

[22] Filed: Apr. 18, 1990

Related U.S. Application Data

[63] Continuation-in-part of Ser. No. 269,265, Dec. 14, 1988, abandoned, which is a continuation-in-part of Ser. No. 136,035, Dec. 21, 1987, Pat. No. 4,925,707.

[51] Int. Cl.5 .............................................. A61K 7/16

[52] U.S. Cl. .................................... 424/405; 424/403; 424/404; 424/78

[58] Field of Search ...................... 523/105, 112, 122; 424/405, 57, 78, 409, 404, 403, 443

[56] References Cited

U.S. PATENT DOCUMENTS 3,161,622 12/1964 Harrington, Jr. et al. ......... 424/443

*Primary Examiner*—Thurman K. Page
*Assistant Examiner*—William E. Benston

[57] ABSTRACT

Stain-resist compositions having antimicrobial activity for treatment of installed carpets are disclosed, as well as processes for applying such compositions. The compositions are useful in simultaneously reducing the bacteria level of the carpet while imparting or improving the carpet's stain-resistance.

2 Claims, 1 Drawing Sheet

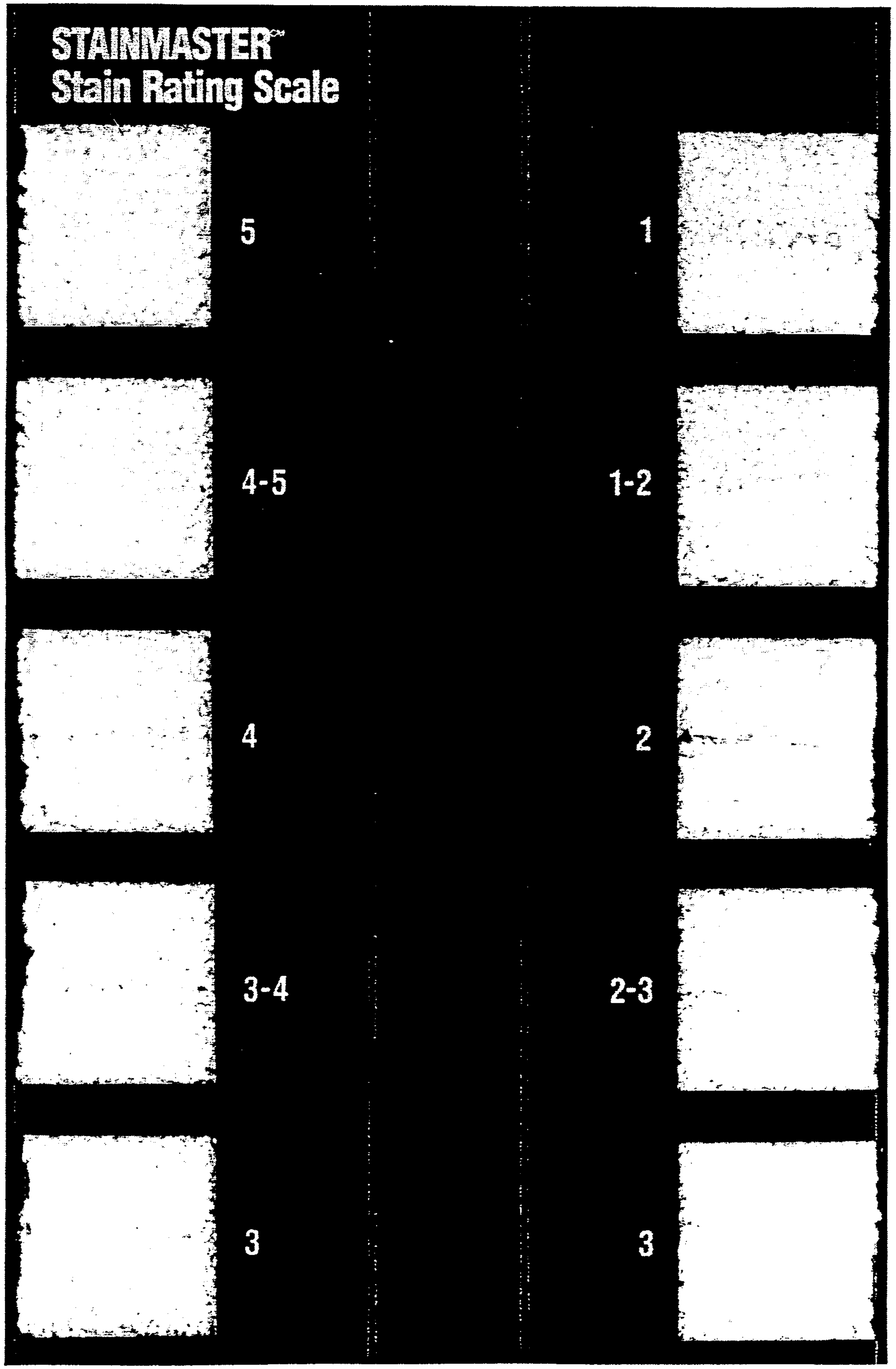
STAINMASTER
Stain Rating Scale
5
1
4-5
1-2
4
2
3-4
2-3
3
3

ANTIMICROBIAL STAIN-RESIST CARPET TREATMENT

CROSS-REFERENCE TO RELATED APPLICATIONS

This application is a continuation-in-part of application Ser. No. 07/269,265, filed Dec. 14, 1988, now abandoned, which was in turn a continuation-in-part of application Ser. No. 07/136,035, filed Dec. 21, 1987, now U.S. Pat. No. 4,925,707.

FIELD OF THE INVENTION

The present invention concerns improvements in and relating to the treatment of carpets, especially those carpets whose pile fibers comprise polyamide fibers, and is more particularly concerned with new compositions and processes that both provide antimicrobial activity and stain-resistance to the carpet by treatment of the carpets in place.

BACKGROUND OF THE INVENTION

Polyamide fibers (generally referred to as nylon) are preferred fibers for use as pile fibers in carpets, and are used for this purpose both in the form of continuous filament yarns, generally bulked continuous filament yarns, and in various forms as cut fiber, often called staple fiber. For many years, both nylon 66 and nylon 6 have been used in large quantities in carpeting; each polymer has its advantages, for certain purposes; as will be noted herein, nylon 6 has a greater affinity for many dyestuffs than does nylon 66. Although there are many different types of nylon carpeting, a conventional type is manufactured by inserting, e.g., plied nylon yarn into a conventional primary backing, e.g., of jute or polypropylene fibers, and then, after dyeing, applying a conventional carpet backing adhesive composition, sometimes referred to as latex, which is adhered also to a secondary backing material, as described, e.g., for a conventional tufted nylon carpet in Ucci, U.S. Pat. No. 4,579,762, issued Apr. 1, 1986. Another type of secondary backing that is frequently used is a foam-backing, i.e. a layer of, e.g., polyurethane foam that can be attached directly to the primary backing without any need for such adhesive. Generally, especially when using carpeting on flooring, in addition to such primary backing, (any adhesive composition) and secondary backing (all underneath the nylon fiber pile), most householders install a conventional underlay or underpad of felted fibers or foam, e.g. of polyurethane, which conventional underlay is generally an entirely separate layer that is not integrally or overall attached to the carpet per se in the same way as the adhesive backing and secondary backing are integrally attached to the primary backing (carrying the nylon pile that is the top or outer surface of the carpet). During commercial manufacture, when such carpets are dyed, the dyeing process is carried out on the nylon pile when it is attached to the primary backing only, i.e., before (any adhesive latex composition and) the secondary backing is secured to the primary backing, and the dyeing process is carried out in conventional manner, e.g., in a beck dyeing machine, generally by a continuous process in which this primary carpet (i.e., the nylon pile and the primary backing only) is immersed in the dye liquor at the boil so as to effect contact and effective and rapid penetration of the dyestuff into the nylon pile, although there are other methods of coloring nylon, e.g., by producer-dyeing, i.e., including pigmentation into the nylon polymer before spinning.

Recently, there has been major commercial interest in imparting "stain-resistance" to nylon fibers and carpets, as described, for instance, in Textile Month, October, 1987, pages 32–34, and several patents are being published on various aspects of imparting stain-resistance to nylon carpets and/or carpet fibers. A major concern of the customer is the durability of the treatment during the various types of treatment that may be encountered during the life of a carpet.

Munk et al., U.S. Pat. No. 4,699,812, issued Oct. 13, 1987, claims a process for imparting stain-resistance to polyamide, wool and silk fibers by contacting the fibers with a solution of an aliphatic sulfonic acid under specified conditions of acid pH and temperature. The primary interest appears to be nylon carpets, but the procedure in, e.g., Example 1 shows vigorous mechanical agitation of a woven nylon 6 fiber "sleeve", in an aqueous solution of a commercial aliphatic sulfonic acid, at a pH adjusted to 2, and at a temperature of 50° C., for 15 minutes, followed by drying with paper towels and in an oven. Variants may be used, at a manufacturing stage prior to the finished product, such as is often done in carpet manufacture; immersing the fabrics, removing excess solution by passing through rollers, and air-drying of the moist fibers at ambient temperature is mentioned; spraying onto the carpet is also mentioned; in particular, the treatment may be during or immediately subsequent the dyeing stage (column 4). Example VII shows that treatment at a pH of 3.8 shows far less improvement in stain resistance than treatment at a pH of 2. Accordingly, a pH between about 1.5 and about 3.0 is said to give more effective results (column 3, lines 56–7). Example III shows that the stain resistance (of Example I) remains after vigorous agitation for 15 minutes at 50° C. in an aqueous detergent solution at a pH of 9.5, rinsing and oven-drying.

Blyth et al., U.S. Pat. No. 4,680,212, issued July 14, 1987, discloses a process of applying a spin finish to nylon fibers during the melt polymerization process by which the fibers are prepared, the finish containing one or more stain blocker(s) in specified amounts. Stain blockers are described and distinguished from fluorochemicals that are used to reduce the tendency of soil to adhere to the fiber. Fluorochemicals are used, however, in combination with a stain-blocker, to improve the durability of stain-resistance imparted by the stain-blocker, in the sense that the carpet retains more stain-resistance after being subjected to much traffic.

Blyth et al., U.S. Pat. No. 4,592,940, issued June 3, 1986, discloses a process of immersing a carpet in a boiling aqueous solution of a selected phenol-formaldehyde condensation product at an acid pH (4.5 or less). The durability of treated carpets is tested variously, including by subjecting carpet samples to two wash cycles in a heavy-duty washing machine using detergent before applying the stain.

Ucci, U.S. Pat. No. 4,579,762, issued Apr. 1, 1986, is referred to above, and claims a carpet having a primary backing coated with an adhesive composition (containing a fluorochemical) and with a pile of nylon fibers (the nylon polymer being modified to contain aromatic sulfonate units). In other words, the stain-resistance is obtained by incorporating stain-resistance into the nylon polymer itself, by chemical modification. The vulnerability of the typical carpet system to water, and the problems caused by the slow process of drying are emphasized in the lower portion of column 1, and at the top of column 2.

Ucci et al., U.S. Pat. No. 4,501,591, issued Feb. 26, 1985, claims a process for imparting stain-resistance during a process for continuously dyeing a carpet, involving adding a silicate and a sulfonated phenol-or napthol-formaldehyde condensation product to the aqueous dye liquor at specified liquor ratios, and then subjecting the carpet to an atmosphere of steam, washing with water and drying. The pH of the liquor in the only Example is 4.5, but is said typically to be in the range of 4.5 to 8 (column 3, lines 22–3). Durability is tested by carrying out a Stain Resistance Test on 5 cm × 5 cm carpet samples alternating with heavy duty cleaning using Steemex commercial units. Ucci, like others, disparages (column 1, lines 46–59) the prior usage of fluorochemicals to minimize staining.

Greschler et al., EP A1 0235989, published Sept. 9, 1987, and corresponding to U.S. Pat. No. 4,780,099, discloses a process for applying sulfonated phenol- or naphthol-formaldehyde condensation products to nylon carpets, after dyeing, in a bath at a pH of between 1 and 2.5, whereby yellowing of the treated articles due to exposure to $NO_2$ is reduced.

Mesitol NBS is mentioned by Greschler as a commercially available material (available from Mobay Chemical Corporation). This is stated in Product Bulletin T.D.S. #1246/1 (Revised) August, 1981, to be an anionic after treating agent and a reserving agent to minimize the staining by selected direct dyes of the polyamide portion in polyamide cellulosic fiber blends, and the "Application Procedures" indicate that the fabric should be treated in a bath. It is understood that stain-blockers are dye-resists or dye-reserving agents such as have long been known and widely used in textile applications, such as resist-printing of nylon fibers. In other words, the mechanism of stain-blocking (in the sense of dye-reserving) has been used for many years.

As indicated in the above patent specifications, and in the analysis in the Oct. 19, 1987, issue of Textile Month, referred to above, hitherto, the emphasis on process techniques, as regards imparting stain-resistance, has been reported to achieve this during the dyeing of the primary carpet, or earlier in the manufacturing process, e.g., by incorporation of modifiers into the nylon polymer, or by engineering or treatment of the fiber itself. So far as is known, prior to the present invention, it had not been disclosed that a significant improvement in stain-resistance could be effective when applied to "in place" carpet that had already been installed with any appropriate secondary backing, and normally also an underpad, as opposed to conventional immersion of the primary carpet in a dye liquor or equivalent application, usually under acid conditions, followed by conventional processing, such as washing, fixing, squeezing, and appropriate drying treatments at elevated temperatures during a manufacturing process.

SUMMARY OF THE INVENTION

It has now been found that a significant improvement in stain-resistance may be effected by applying stain-blockers to install carpets, in contrast with the immersion or other manufacturing treatments that have been referred to, and that the results of this in-place treatment have been acceptable to a surprising extent.

Accordingly, there is provided, according to the invention, a process of imparting stain-resistance to an installed nylon carpet by a process that includes the steps of treating the installed nylon carpet, especially a carpet of nylon 66 fiber, by applying thereto a stain-blocker in sufficient amount and in such manner as to obtain a significant improvement in stain-resistance, and of allowing the treated carpet to dry in the atmosphere.

The process of the invention is described in more detail and with preferred embodiment hereinafter, and is expected to have considerable commercial significance, as will be described. For instance, a preferred commercial application is expected to be overall treatment by appropriately-trained personnel to obtain the type of professional appearance that a customer normally expects. This is expected to be especially useful when applied as a supplement to stain-resist and/or soil-resist treatments that have already been applied during the manufacturing process, as described in the prior art referred to already. However, overall treatment of carpets that have not been treated with stain-blocker (during manufacture or otherwise) is also feasible, and may prove useful, also. These types of overall treatment, to give an appearance that is commercially acceptable, are generally to be preferred in contrast with spot or localized treatments such as may result from application topically to an installed carpet by use of a spray can. However, as will be seen, spot cleaning with detergents may affect the durability of stain-resist performance, so that certain topical applications to installed carpets may be advantageous, depending on circumstances.

It has been found that a significant improvement and a satisfactory commercially-satisfying appearance could be obtained by the process of the invention, i.e., application to an installed carpet, (especially to deep pile carpets with a pile height of about ¼-inch or more, more particularly ½-inch, or ¾-inch or more) since there has been a prejudice in the trade against this technique and in favor of application during the manufacturing process, as indicated hereinbefore, e.g., by Ucci.

It has also been discovered that stain-resistance may be imparted to an in-place nylon carpet whose stain-resistance has been reduced due to treatment with some antimicrobial agents, including commonly-used household disinfectants, and/or with deodorizers. Such treatments, when applied to a stain-resistant carpet, tend to destroy or substantially diminish the stain-resistance. By applying a stain-blocker after treatment with such products, the stain-resistance of the disinfected and/or deodorized carpet can be restored and even improved. This embodiment may also serve, of course, to impart stain-resistance to an in-place carpet which was not previously stain-resistant.

A further embodiment of the invention involves aqueous stain-resist compositions capable of both imparting to (or improving the stain-resistance of) an in-place carpet and which also have antimicrobial activity. Such compositions are comprised of an effective amount of both a stain-blocker and an antimicrobial agent, the latter preferably being glutaraldehyde. By application of such compositions to an installed carpet according to a process of this invention, the two-step process described above of applying the antimicrobial agent prior to the stain-blocker can be consolidated into a single application step, thereby simultaneously applying the antimicrobial agent along with the stain-blocker without having either interfere with the efficacy of the other.

BRIEF DESCRIPTION OF THE DRAWING

The file of this patent contains at least one drawing executed in color. Copies of this patent with color drawing(s) will be provided by the Patent and Trademark Office upon request and payment of the necessary fee.

The FIGURE is a color photograph to show the Stain Rating Scale that was used herein.

DETAILED DESCRIPTION OF THE INVENTION

The treating step must be carried out in such manner and with stain-blocker in sufficient amount that a significant improvement in stain-resistance is obtained. It is believed that a significant increase in stain-resistance will be readily apparent to a skilled person with the aid of a suitable test. As will be recognized by those experienced in the treatment of nylon carpets, however, the precise treatment conditions that may be necessary will depend on the nature of the carpet, e.g., its construction (various features being mentioned herein), the type of nylon fiber used, and the stain-resistance of the nylon fibers in the pile before commencing the treatment. Experience in determining suitable conditions can be obtained empirically in conjunction with the information contained herein, especially in the Examples. Stain-resistance may be determined, if desired, by any of a number of published tests, but herein, stain-resistance levels are measured according to Stain Test 1, unless stated otherwise. Generally, the starting carpet (i.e., the carpet before treatment) will be treated because it is considered to have insufficient stain-resistance. As will be shown hereinafter, however, detergent-cleaning and wear can reduce the stain-resistance of a carpet, at least so far as the durability of the stain-resistance is concerned. Accordingly, even if a starting carpet already passes a recognized test for stain-resistance, an improvement in stain-resistance, at least in the sense of the durability of the stain-resistance, may be obtained by in-place treatment with stain-blocker as described herein (it being understood, however, that it may be undesirable to build up too much coating of stain-blocker, e.g. for aesthetic reasons). However, for most purposes, according to the present invention, since a starting carpet will generally have inadequate stain-resistance, as can be shown by a stain-rating of 4 or less (as described hereinafter with regard to Stain Test 1, with staining for 30 minutes) a significant improvement in stain-resistance can be demonstrated for the purposes of the present invention by improvement from such a stain-rating of 4, to a stain-rating of 5. As will be shown in some Examples, however, it is possible to improve carpets by using the process of the invention from even lower starting stain-ratings, and such more effective treatments are generally preferred. For instance, a much improved stain-resistance can be shown using a longer staining time of 24 hours for Stain Test 1, and improving from a stain-rating of 4 to 5, and treatments to obtain this are preferred. Once appropriate treatment conditions have been established for any particular type of carpet, using as starting carpet a sample having a low stain-rating, and improving to the desired high stain-rating, preferably of 5, and thus determining that a significant improvement in (or much improved) stain-resistance is obtainable using such conditions, including the amounts of stain-blocker and conditions for that particular type of carpet, equivalent treatment conditions may be applied, according to the invention, including to starting carpets having a higher stain-rating, and even a stain-rating or 5, so as to improve the durability of the stain-resistance by treatment according to the invention. Thus, as indicated, although other staining tests may be perfectly satisfactory, and even preferred by some operators or for certain purposes, for ease of understanding and consistency throughout the remainder of this specification, it will be understood that references to stain-ratings herein will be to this Stain Test 1.

STAIN TEST 1

In this standardized Stain Test 1, each carpet specimen is first stained and then spot cleaned by hand in an attempt to remove the stain, and the various samples are then compared. As will be apparent, essentially the same procedure is used, but the duration of the staining period may be increased so as to increase the severity of the staining test. The staining agent is cherry-flavored, sugar-sweetened "Kool-Aid" (sold commerically), mixed in amount 45 gms (±1) of "Kool-Aid" in 500 ccs water, and allowed to reach room temperature, i.e., 75° F. (±5) or 24° C. (±3), before using.

The specimen is placed on a flat non-absorbent surface, 20 ml of "Kook-Aid" are poured onto the carpet specimen from a height of 12 inches (30 cm) above the carpet surface, and the specimen is then left undisturbed for a staining period that may be, e.g., 5 min., 30 min. or 24 hours, according to the desired severity of the test. (Although the 5 min. staining period is not referred to in the Examples herein, earlier tests have used a staining period as short as this.)

Excess stain is blotted with a clean white cloth or clean white paper towel or scooped up as much as possible, without scrubbing. Blotting is always performed form the outer edge of spill in towards the middle to keep the spill from spreading. Cold water is applied with a clean white cloth or a sponge over the stained area, gently rubbing against the pile from left to right and then reversing the direction from right to left. The excess is blotted.

A detergent cleaning solution (15 gms (±1) of TIDE detergent mixed in 1000 cc of water, and also allowed to reach room temperature before using), is applied with a clean white cloth or a sponge directly tot he spot, gently rubbing the pile from left to right and then reversing the direction from right to left. The entire stain is treated, all the way to the bottom of the pile, and then the blotting is repeated.

The cold water treatment is repeated, and the carpet is blotted thoroughly, to remove the stain and also the cleaning solution, so the carpet does not feel sticky or soapy.

The cold water and detergent cleaning steps are repeated until the stain is no longer visible, or no further progress can be achieved. The carpet is blotted completely to absorb all the moisture.

The stain-resistance of the carpet is visually determined by the amount of color left in the stained area of the carpet after this cleaning treatment. This is referred to as the stain-rating, and is herein determined according to the Stain Rating Scale (that is illustrated in the FIGURE, being a photograph of a Stain Rating Scale) that is currently used by and available from the Carpet Fibers Division of E. I. du Pont de Nemours and Company, Wilmington, Del. 19898. These colors can be categorized according to the following standards:

5=no staining

4=slight staining

3=noticeable staining
2=considerable staining
1=heavy staining

In other words, a stain-rating of 5 is excellent, showing excellent stain-resistance, whereas 1 is a bad rating, showing persistence of heavy staining. As will be understood, and shown hereinafter in the Examples, even an improvement in stain-rating from 1 to 3 (after a 30 min. staining period) shows a significant increase in stain-resistance. As can be seen from the Stain Rating Scale, a dramatic difference in color is shown by changes in stain-rating at these low levels, while it is recognized that it is generally more difficult to improve stain-ratings above 4.

Suitable stain-blockers that may be used according to the invention include those described in Blyth et al., U.S. Pat. No. 4,680,212, and the sulfonated condensation products described (as stain-resist agents) in Greschler et al., EP Al 0235 989, and the improved materials, being acetylated or etherified sulfonated phenol-formaldehyde condensation products referred to in EP Al 0235 980, published Sept. 9, 1987, and corresponding to copending Application Ser. No. 943,335, filed Dec. 31, 1986, in the name of Liss (directed to synthetic polyamide textile substrates, such as carpeting, treated with such improved condensation products, so as to impart stain-resistance to the substrate without suffering from a yellowing problem associated with prior art materials) and also the compositions listed in copending Applications (Ser. No. 07/136,033 and Ser. No. 07/136,038), filed simultaneously with the parent of this application (Ser. No. 07/136,035), all of which are hereby included by reference herein. To avoid any misunderstanding, a staining agent itself is not regarded as a "stain-blocker" (as the term is used herein) as the objective is to achieve stain-resistance and to avoid or minimize color changes in the carpet, as a result of treatments according to the invention.

As indicated in the Background above, and in the prior art referred to, the term stain-resist agent has sometimes been used broadly to include fluorochemicals that should be and are herein more correctly described as soil-resist agents, whereas the term stain-blocker has been and is herein used more narrowly to exclude soil-resist agents that do not have the capability of resisting staining by red food dyes such as found in "Kool-Aid", e.g. Red Dye No. 40.

In addition to treatment of the installed nylon carpet with a stain-blocker, in accordance with the present invention, the durability of the stain-resistance may be improved by treatment of the installed carpet with a compound to improve the anti-soiling characteristic, especially a fluorochemical (sometimes referred to as a stain-resist agent) as described in Blyth et al., U.S. Pat. No. 4,680,212 and herein, and in the other references that are mentioned herein, and that are incorporated herein.

As described herein, and more particularly in the Examples, different materials may be applied in combination, being applied from a common aqueous or other carrier, or separately.

As described more particularly hereinafter, in the Examples, the efficacy of the stain-resistance that is imparted is generally improved by improving the overall distribution and opportunity for contact between the nylon fibers and the materials applied, especially by achieving thorough and essentially uniform overall wetting of the nylon fibers, especially reaching down to impart stain-resistance to the base of the pile fiber, as far as will be visible, during normal wear, and when the pile fibers are parted for any reason. This is generally and most conveniently achieved by applying an aqueous detergent solution to achieve the desired objective of overall and thorough wetting of the nylon pile fibers, and preferably by mechanical working to improve contact, distribution and penetration, e.g., by a pile brush operated by hand or automatically, for instance using a cleaning device such as may be available commercially. Application of a detergent solution may conveniently be achieved by first cleaning the carpet, e.g., using a cleaning machine that is commercially available with a detergent that is sold for such purpose, especially if the carpet is initially in soiled condition, and then, while the carpet fibers are still in moist condition, the stain-blocker (and fluorochemical soil-resist agent, if desired) may be applied and preferably worked into the carpet. However, as indicated hereinafter, good results have also been achieved by applying the stain-blocker together with a detergent.

As indicated, it will generally be desirable to apply materials in such way as to avoid or minimize shade changes and spotty results, such as would result from inappropriate and/or uneven application. However, as indicated elsewhere, spot cleaning or other topical-type cleaning can reduce the stain-resistance that has already been imparted to nylon fibers, and so can remove some of the effectiveness of any existing stain-blocker on the fibers, and this may make it desirable to apply spot or other topical applications to achieve as uniform and overall result as possible on the installed carpet. It will be understood that the term overall is used herein in contrast to spot or localized applications.

An essential feature of the present invention, as it will be applied in commercial practice, is treatment of the installed carpet in place, i.e., without removal of the carpeting from the floor or whatever location is normal (although it will be understood that, for testing purposes, e.g., in the laboratory, carpets and samples of carpeting can and will be treated in other locations), as opposed to treatment of a carpet (or precursor nylon fiber or even polymer) by a stain-blocker by immersion or otherwise during a manufacturing process. Accordingly, depending on the location of the installed carpet, and the surrounding environment, it will generally be desirable to use appropriate conditions and precautions, e.g., limiting the amount of water, since drying of the treated carpet will generally not be so easily achievable as during a manufacturing process. However, an advantage of treatment of an installed carpet is that (depending on the convenience of the owner of the carpet) the stain-blocker may be left in contact with the nylon fibers for a longer period, overnight, or even over a weekend, than would be practical in most manufacturing processes. This feature means that some limitations that may have been applicable in practice to limit the use of potential known dye-resist agents (as potential stain-blockers) may not apply for use according to the present invention, and broadens the scope of applicability of the present invention to other stain-blockers that have not been used hitherto in the manufacturing process. It is of the essence of the present invention that the treated carpet cannot be dried in an oven, as have been the case after application of stain-blockers in a manufacturing process. Accordingly, the treated carpet is allowed to dry in the air, but it will generally be preferable to assist the drying of the treated carpet by blowing hot air through the pile of the installed carpet. As indicated, it will generally be desirable to allow the stain-blocker to remain in contact with the nylon fibers in moist condition for several hours, e.g., at least six hours, and preferably overnight, before completing the drying of the treated carpet, e.g., by blowing hot air.

As can be seen from the Examples herein, significant improvements in stain-resistance have been obtained according to the invention by treatment with stain-blocker at normal to alkaline pH values, e.g., from pH values of about 7 up to about 11. This is contrary to what has been indicated in the art, where emphasis has been on the advantages of applying stain-blockers under acidic conditions, and usually at pH values of less than 5, and sometimes at acidic pH values much less than 5. Although it may be possible to treat the carpets at such acidic pH values, depending on the environment of the installed carpets, the treatment step according to the present invention will generally be preferably carried out at pH values that are not too far from normal, e.g., from about 4 to about 11, even though a value of about 6 or more is generally to be preferred over more acid pH values.

Additional processes of this invention relate to the application of antimicrobial agents and/or deodorizers to in-place nylon carpets followed by the application of a stain-blocker, optionally in combination with a soil-resist agent such as a fluorochemical. Many antimicrobial agents, including common household disinfectants, and deodorizers, when applied to nylon carpets, destroy or significantly neutralize any stain-resistance the carpet may have had. The subsequent application of a stain-blocker renews the stain-resistance of the carpet or imparts such properties to carpets never previously having been stain-resistant.

The term "antimicrobial", as used herein, refers to broad spectrum agents which are active against most bacteria, against insects, fungi and odors caused by bacteria and germs. The term also encompasses common mildewcides, disinfectants, bactericides, fungicides and insecticides. Such compounds may be classified either as "non-residual", most commonly quaternary ammonium compounds which kill on contact and have no residual effect, or as "residual" agents which do remain active for a finite period of time after application. Both classes of compounds generally rely upon cationic active ingredients; thus when they are applied to a nylon carpet whose fibers have previously been treated with stain-blockers which are anionic in nature, the stain-resistance is largely neutralized. Antimicrobial agents are typically applied to nylon carpets either topically or by injection through the carpet-backing. (In the latter case, the carpet is first lifted from the underpad in the area where the agent is to be injected.) Antimicrobials are commonly used on carpets as disinfectants to kill bacteria or other targets introduced into the carpet by a wide variety of sources, including, for example, water damage, sewer back-up, uncleaned spills, pet excretions, etc.

The term "deodorizer" or "deodorizing agent", as used herein, refers either to compounds containing merely a perfume or a similar substance used to mask odors or to an active material which usually is comprised of both an odor masker and a small amount of one or more antimicrobial agents, typically a disinfectant. Deodorizers too——particularly cationic types——have a neutralizing effect on stain-resistance.

It has now been found that in-place nylon carpets may be disinfected and imparted with stain-resistance by first wetting the carpet, applying an antimicrobial agent to the carpet, and then, while the carpet is still moist, applying a stain-blocker to the pile fibers in sufficient amount and in such manner as to obtain significant improvement in stain-resistance, following which application the carpet is allowed to dry in the atmosphere.

Similarly, in-place nylon carpets, the fibers of which have previously been treated with a stain-blocker, may be disinfected and imparted once again with stain-resistance by first wetting the carpet, applying an antimicrobial agent, then, while the carpet is still moist, applying a stain-blocker, which is mechanically worked into the nylon fibers of the pile of the carpet so as to improve the distribution and contact between the stain-blocker and the nylon fibers of the pile of the carpet, the stain-blocker being applied in sufficient amount and in such manner as to obtain a significant improvement in stain-resistance. The carpet, thus treated, is then allowed to air-dry.

The process may optionally be modified by applying an aqueous mixture of a soil-resist agent (such as a fluorochemical) and a stain-blocker in place of the stain-blocker alone, or by applying the soil-resist agent and the stain-blocker to the carpet separately.

In all these processes a quantity of antimicrobial agent sufficient to disinfect the area of the carpet being treated should be used, and the agent should be applied in accordance with the manufacturer's recommendations.

The wetting step described above serves to promote effective distribution of both the antimicrobial agent and the stain-blocker. Wetting is preferably achieved by steam-cleaning, though other means such as wet-vacuuming, shampooing or simply applying water may also be used. In the event the carpet to be treated is already wet or moist as, for example, from water damage, the wetting step may be omitted.

Alternative processes involving the application of the antimicrobial agent prior to or simultaneously with the wetting or steam-cleaning of the carpet are also effective.

As an alternative to such sequential processes involving separate application of the stain-blocker and the antimicrobial agent, new aqueous stain-resist compositions having antimicrobial activity have now been found. Such compositions are comprised of an effective amount of both a stain-blocker and an antimicrobial agent. As used in such compositions, the term "antimicrobial agent" refers to anionic or non-ionic agents capable of reducing a representative microbial population associated with carpets by at least 90% within one hour when applied to an in-place carpet either topically or via injection through the backing. A "representative microbial population" refers to the combination of *Staphylococcus aureus* ATCC 6538, *Entrerobacter aerogenes* ATCC 13048, and *Pseudomonas aeruginosa* ATCC 15442 (U.S. Environmental Protection Agency, "Efficacy Data Requirements for Carpet Sanitizers"), or naturally occuring bacterial populations such as the bacterial population associated with canine urine. The most preferred antimicrobial agent is the non-ionic glutaraldehyde, while a preferred anionic agent is phosphoric acid. Optionally the compositions may also contain soil-resist agents (such as fluorochemicals), silicon-based water-repelling compounds, and/or deodorizers which are compatible with, i.e. do not destroy the efficacy of the stain-blocker and the antimicrobial.

It is believed that all known stain-blockers will be effective in such compositions, in that such materials are invariably anionic in nature and thereby compatible with non-ionic or anionic antimicrobial agents. The group of stain-blockers previously discussed in this specification, sulfonated phenol-formaldehyde condensate polymers, sulfonated naphthol-formaldehyde condensate polymers or hydrolyzed vinyl aromatic-maleic anhydride polymers, plus combinations of any two or more of these, have been found to be particularly effective.

The minimum quantities of both the stain-blocker and the antimicrobial agent will, of course, vary with the specific materials involved, the desired level of stain-resistance, and the variety and concentration of the microbial population. As the level of antimicrobial in the composition is increased, safety considerations——both as to application of the agent and removal of any excess following application——come into play. It is particularly desirable to limit the amount of antimicrobial to that necessary to provide efficacy during the treatment period, leaving no unconsumed, residual agent on the carpet. This minimizes inhalation of the agent or skin irritation which may be caused by exposure to a large excess of residual agent. It has been found that this result can generally be achieved by using compositions containing 200 ppm of glutaraldehyde and applying those compositions to the carpet at rates between one-half gallon and one gallon per 100 sq. ft. of carpet, depending on the carpet construction and the severity of the contamination.

These compositions may be applied according to the following processes. The compositions are applied to the carpet in sufficient quantities and in a manner to ensure thorough wetting of the carpet pile from the tips of the carpet tufts down to the backing. Such wetting can be enhanced by raking the carpet after application, by use of a pile brush or other forms of agitation, or merely by waiting an adequate period of time to ensure migration of the aqueous composition through the pile. Subsequently, one should allow the composition to remain in contact with the carpet for a sufficient period of time for the antimicrobial agent to take effect. This will, of course, vary with the specific antimicrobial agent, the quantity applied, and the population involved, but is generally between 5 minutes and one hour. If there is no or little residual antimicrobial agent, the carpet can be allowed to dry "as-is" with no further cleaning. Alternatively the carpet can be cleaned to remove residual antimicrobial agent, with hot-wet extraction being the preferred cleaning method.

To both deodorize and impart stain-resistance to an in-place nylon carpet, an aqueous solution of a stain-blocker and a deodorizing agent is applied to the carpet, the pile fibers are mechanically worked so as to improve the distribution and contact between the stain-blocker and the nylon fibers of the pile, the stain-blocker being applied in sufficient amount and in such manner as to obtain a significant improvement in stain-resistance. Finally, the carpet is allowed to air-dry.

It should be noted that in this process the deodorizer serves only to mask odors. To be effective as a disinfectant, any cationic active ingredient found in the deodorizing agent would have to be applied prior to the stain-blocker.

Just as with antimicrobials, deodorizers should be applied in accordance with manufacturer's recommendations and in sufficient quantities to deodorize the area of the carpet being treated.

Just as many antimicrobial and deodorizing agents serve to reduce stain-resistance, other treatments may have a similar deleterious effect. Examples of such treatments include re-dyeing of an in-place carpet, application of high pH (10 or more) pre-sprays used to quickly neutralize highly soiled areas, use of some silicone-containing soil-resist agents, and use of certain insecticides. In each of these cases, a significant improvement can be obtained in the stain-resistance of such carpets after any such treatment. With respect to dyeing, the improvement can be attained whether the carpet is first redyed and then treated with the stain-blocker or alternatively if the stain-blocker is mixed with the dye and applied simultaneously.

In all these cases, as with the processes for disinfecting or deodorizing the carpet prior to imparting stain-resistance, the preferred classes of stain-blockers are sulfonated phenol-formaldehyde condensate polymers, sulfonated naphthol-formaldehyde condensate polymers or hydrolyzed vinyl aromatic-maleic anhydride polymers. Combinations of any two or more of these stain-blockers may also be used.

The invention is further illustrated in the following Examples, in which all parts and percentages are by weight, o.w.f. is estimated weight of indicated active ingredient on weight of (nylon face) fiber, and the nylon is 66 nylon, unless otherwise indicated, and approximate metric equivalents are given.

EXAMPLE I

A bcf (bulked continuous filament) nylon 1110-68 yarn, i.e. 1110 denier (1235 dtex) and 68 filaments (of trilobal cross-section), was produced by a conventional process. Two of these yarns were plied and twisted to produce a yarn having a balanced twist of 4.5 tpi (turns per inch, 1.8 turns per cm). The resulting yarn was then heat-set at 270° F. (132° C.) in a Superba heat-setting machine. A cut pile tufted carpet was constructed from the heat-set yarn and a conventional polypropylene primary backing to the following specifications: —42 oz/sq yd; ½ inch pile height; 1/10 gauge; 31 stitch rate per 3 inches (1.4 Kg/sq m; 13 mm; ¼ cm; 41/100 cm). This carpet was dyed (to a light beige shade) and finished, using a conventional batch dye process, dye auxilliaries and the following dye formula, based on weight of carpet, 0.011% C.I. Acid Yellow 219, 0.0094% C.I. Acid Red 361, 0.008% C.I. Acid Blue 277 at a pH of 6.5. After dyeing, this carpet was rinsed. A commercial fluorochemical (equivalent to cationic version of "Teflon" Toughcoat, available from E. I. du Pont de Nemours and Company, Wilmington, Del. 19898, was applied (0.9% o.w.f.) in a conventional spray application, and the carpet was dried in an oven. A commercially available latex composition (Textile Rubber Co., Calhoun, GA) was applied as a carpet backing adhesive, with a secondary polypropylene backing under the Tradename "Actionbac" (Amoco, Atlanta, GA).

This "finished carpet" with latex and secondary backing was then used as a specimen for "in place" treatment with a stain-blocker. A 20g/1 solution of an acetylated Mesitol NBS solution as referred to in copending Application Ser. No. 943,335, mentioned above, was used for the stain-blocker solution (adjusted to pH 5.0 with citric acid) and was uniformly applied at approximately 0.5% of active stain resist o.w.f. by spraying at room temperature (using a Sears brand, 2 gallon (about 7.5 liter) capacity open top sprayer). The sprayed mixture was worked into the pile fiber using a pile brush. The treated carpet was allowed to dry at room temperature.

Samples of the dried carpet were then tested by staining for 30 min., using "Kool-Aid", according to Stain Test 1. Untreated (control) samples of the same carpet, (i.e., without the stain-blocker treatment) were also tested, for comparative purposes The treated carpet samples showed only a noticeable pink stain on the fiber, after cleaning, i.e. a stain-rating of 3, in contrast to dark red staining (i.e. a stain-rating of 1) on the untreated carpet samples Although even this stain-rating (3) would not be acceptable for this half inch pile carpet, there was significant improvement in stain-resistance, in comparison with the rating (1) for the untreated carpet, and it will be understood that by changing the treatment conditions for the same carpet, or by applying the same treatment to a different carpet (e.g., with a less dense, shorter pile, Suessen set, staple carpet, providing greater accessibility for the stain-blocker), more effective stain-blocking can be expected, and obtained, as will be seen hereinafter.

A similar result has been obtained by using Mesitol NBS solution itself, i.e. the non-acetylated material, in similar amounts and under similar conditions.

EXAMPLE II

This carpet was similar to that in Example I, except that the yarn was 3.0s (5.1 m/g) cotton count, 3.8 tpi (1.5 turns per cm) and Suessen set at 200° C., and the carpet was 45 oz/sq yd (1.5 Kg/sq m) and 24 stitches per 3 inches (31/10 cm), and Scotchgard Fluorochemical FC 393 was applied instead of the fluorochemical used in Example I. When this carpet was treated with the same stain-blocker and tested under similar conditions as in Example I, it gave only a slight pink stain (rating 4), in contrast to the dark red staining for the untreated carpet.

EXAMPLE III

A sample of the finished carpet, as prepared in Example II, was placed on a padding material (Metrix 100, prime urethane carpet cushion of ¼ inch (6 mm) thickness, sold by General Felt Industries & Co.) to simulate the conditions of a typical carpet "in place", for in-home use, and then cleaned with 4 passes of a Chemco brand soil extractor model 60DM, (available from Accommodation Sanitary Supply Co., Philadelphia, PA) using Spartan X-Traction II detergent solution (a standard detergent composition also available from Accommodation Sanitary Supply Co.) diluted 1:53 in room temperature water. The damp carpet (estimated 10–20% moisture level) was then sprayed with a mixture containing "Teflon" MF (Du Pont brand fluorochemical): acetylated Mesitol NBS, as in Example I: water in 1:1:15 proportions at a pH of 5.0 using a pressurized sprayer, 2 gallon (7.5 liters) capacity (brand name "Aconoline", sold by B & G Equipment Co.) in approximate amount of active stain resist estimated to be 1% o.w.f. The sprayed mixture was then worked into the pile fiber using a pile brush as in Example I. The treated carpet was allowed to dry in air and then stain tested as described in Example I, except that the staining solution remained for 24 hours before cleaning. The treated carpet showed no visible stain (stain-rating of 5) compared to untreated carpet (a dark red stain with a stain-rating of 1).

This Example shows the improved effect achieved by uniform distribution of stain resist throughout the pile fiber by spraying the carpet while still moist after detergent-cleaning.

EXAMPLE IV

This is similar to Example III, except that 8 cleaning passes were performed with the Chemco soil extractor, the cleaning detergent solution consisted of 1 part of the Spartan X-Traction II detergent mixed with 0.2 parts of the same stain-blocker as in Example I, with a resultant pH of 7.5, and the approximate amount of active stain resist was estimated to be 0.8% o.w.f. This treated carpet showed no visible stain (stain rating of 5) compared to untreated carpet (a dark stain with a stain rating of 1).

This Example shows effective distribution of a stain-blocker throughout the pile fiber by cleaning a carpet 30 with a detergent solution containing the stain-blocker.

EXAMPLE V

A commercial or contract type carpet was used instead of the residential carpet constructions in the earlier Examples. Du Pont "Antron" XL, 1280 denier (1420 dtex) fiber with a hollow cross-section was used for this carpet. The construction specifications were 40 oz/sq yd (1.4 Kg/sq m), 5/16 inch (8 mm) pile height, dyed to earth-tone beige color, using leveling acid dyes followed by the same fluorochemical as in Example I. The carpet was then latexed and glued down on a linoleum padding. The carpet was placed in a corridor and subjected to wear for 178,000 foot traffic cycles. The carpet was then cleaned with Clarke's heavy duty steam extraction unit model Ext-20 (available from Advance Paper Co., Wilmington, DE) and dried at room temperature. The dried carpet was then sprayed with the same stain-resist solution at room temperature in the same way as explained in Example I, except the active stain resist was approximately 1.7% o.w.f., the sprayed mixture being worked in using a pile brush. Samples of the dried carpet were then stained for 30 min. by Stain Test 1. The treated carpet showed no stain (stain-rating of 5) compared to untreated carpet (a dark stain with a stain-rating of 1).

EXAMPLE VI

The starting carpet was a finished carpet (nylon staple cut pile 40 oz/sq yd, (1.4 Kg/sq m) ½ inch (13 mm) pile height, beck dyed to light beige shade, latexed and secondary backed) that had already been mill-processed with an effective amount of the stain-blocker used in Example I during manufacturing, and had been stain tested using Stain Test 1 (24 hours) to show a visual stain-rating of 5. This carpet was then subjected to 344,000 foot traffic cycles.

The trafficked carpet was cleaned using a detergent and a Stanley Steemer (Dublin, Ohio) truck mount unit and some of this was dried. The dried carpet was stained for 24 hours and cleaned using Stain Test 1, and now showed noticeable staining (visual stain-rating of 3).

Part of the carpet that was cleaned, but which was still partially damp (estimated to be about 10% moisture level) was oversprayed with the same stain-blocker as in Example I, in a detergent solution (Stanley Steemer #SS76, a standard anionic detergent) at a pH of 7.8 (to a concentration of about 0.4% o.w.f. active stain-resist), followed by "Teflon" MF fluorocarbon spray application. The sprayer used in this case was a 2 gallon capacity can with Spray System Tip TEEJET 8004 (Spraying System of Almoca Corp., Wynnewood, PA), 40–60 psi and an application height of 12–19 inches above the carpet, 2 passes, one in each direction. This treated carpet was air-dried at room temperature and then stain-tested for 24 hours using Stain Test 1. The carpet showed no visible stain with a stain-rating of 5.

This Example shows that a stain-blocked carpet with a stain performance that has been reduced (stain-rating of 3) because of detergent-cleaning and trafficking, can be restored to its original stain-performance (stain-rating 5) with an in-place treatment as described above.

EXAMPLE VII

A 15 dpf, trilobal cross-section, staple nylon 66 was produced by a conventional process. The yarn was prepared as 3s cotton count, 2 ply balanced twist of 4 turns per inch and Suessen heat set (200° C.). The carpet was constructed with the following specifications: 1/10 inch gauge, 46 oz/sq yd, ½ inch pile height, beck dyed to a light beige shade with the standard dyeing auxilliaries and level acid dyes. After dyeing, the carpet was treated in a bath containing 2.5% o.w.f. of the same stain-blocker as in Example I at 170° F. for 20 min. at approximately 20:1 liquor ratio. The carpet was then rinsed, topically treated with a cationic dispersion of the fluorochemical described in Example 6 of EP A2 172,717, and dried, latexed, cured and tip sheared. The carpet was stain-tested for 24 hours using Stain Test 1 and visually rated a stain-rating of 5. Half this cleaned carpet was re-tested by restaining on part of the same spot for 30 minutes using Stain Test 1. The stain-rating was now slight staining (i.e., a rating of 4). The remaining half of the carpet was sprayed with the same stain-blocker as in Example I at 0.16% o.w.f., and allowed to dry at room temperature. This treated carpet was then stain-tested similarly for 30 minutes using Stain Test 1, to give a stain-rating now of 5 again.

This Example shows that a sample with a reduced stain-performance, because of detergent-cleaning, can be restored to its earlier stain-performance by an in-place treatment.

EXAMPLE VIII

A stain-resist-treated, cut pile saxony carpet was produced from a 13 dpf, bcf, trilobal cross-section (1107 total denier) Superba heat set yarn. The latexed and finished carpet with a secondary polypropylene backing was tested per Stain Test 2 (described below) and was found to have an inadequate stain rating of only 2–3, indicating that the stain-resist-treatment was not satisfactory. The carpet was cleaned with a Chemco brand soil extractor model 60DM (1 pass) with a 1:100 diluted shampoo blend (as disclosed in Example 2 of copending application (Ser. No. 07/136,033), filed simultaneously herewith), and referred to above, at a pH of 7.7 followed by an overspray of a mixture of the 80:20 hydrolyzed styrene/maleic anhydride polymer: acetylated Mesitol NBS, as described in Example 1 of the same copending application (Ser. No. 07/136,033): "Teflon" MF: water in 1:1:46 proportions (2 passes). The carpet was treated in this manner "in place" at room temperature and was allowed to dry at room temperature. This dried treated carpet showed no visible stain (stain-rating of 5) when tested by Stain Test 2 (24 hours).

The carpet can be treated in this manner by multiple passes, with such a diluted shampoo, followed by an overspray, as described, to improve the stain-rating of a wide range of inadequately stain-resist-treated, or untreated carpets.

STAIN TEST 2

A 6 inch (15 cm × 15 cm) specimen of carpet is placed on a flat non-absorbent surface. 20 ml of the "Kool-Aid" solution prepared as for Stain Test 1 described herein is applied to the specimen of carpet by placing a 1½ inch–2 inch (3.8 cm–5.1 cm) cylinder tightly over the specimen and pouring the "Kool-Aid" solution into the cylinder to contact the carpet specimen thereby forming a circular stain. The cylinder is then removed and excess "Kool-Aid" solution is worked into the carpet tufts to achieve uniform staining. The stained carpet specimen is left undisturbed for 24±4 hours, after which it is rinsed thoroughly with cool water, squeezed dry, and excess solution removed. The specimens are inspected an evaluated according to the same rating standards as described hereinabove for Stain Test 1.

EXAMPLE IX

This Example illustrates a preferred procedure for treating soiled carpets "in place", regardless whether they may or may not have been first cleaned with an anionic shampoo, which may or may not have contained a stain-resist agent, such carpet having been soiled or trafficked as may happen in normal residential use.

A beige-colored, mill-processes, latexed and secondary backed carpet was made form bcf 2-ply Superba heat set and 38 oz/sq. yd (1.3 Kg/sq m) with a finished pile height of about 7/16 inches (11 mm). The carpet was stained using Stain Test 2 and was found to have a stain-rating of 1–2. The carpet was cleaned with a Stanley Steemer truck mount unit (4 passes) using Stanley Steemer #SS76 brand shampoo (pH 8.8). The cleaned carpet was then further cleaned using the same shampoo blend as in Example VIII, but with a final dilution of 1:150 in water and 4 passes, followed by an overspray (2 passes) of the same blend as in Example VIII: "Teflon" MF: Water in the same 1:1:46 proportions. The carpet was allowed to dry at room temperature. This dried treated carpet showed no visible stain (stain-rating of 5) when tested by Stain Test 2 (24 hours).

EXAMPLE X

A carpet as describe in Example IX has also first been cleaned with a commercial shampoo (predominantly anionic, without cationic materials) and then followed by either (1) cleaning wit the same shampoo blend and an overspray as described in Example IX or (2) just the overspray as described in Example IX (but with multiple passes, instead of only 2 passes), or (3) cleaning with anionic shampoo materials containing the stain-blocker, to give satisfactory high stain-ratings.

As indicated, nylon 6 has a greater affinity for many dyestuffs than nylon 66. This means that, for a nylon 6 carpet, a greater amount of stain-blocker may generally have to be used to obtain equivalent improvement in stain-resistance (equivalent to that obtained as shown herein for nylon 66 carpets), or more passes (repeats of the application treatment) may have to be used. This means that more coating may build up on the nylon fiber, and may affect (adversely) the aesthetics of the carpet and face fiber. Accordingly, the treatment of the invention is preferably applied to carpets whose fiber has already received treatment with stain-blocker during manufacture of the carpet and/or fiber, especially, as indicated, for nylon 6.

EXAMPLE XI four commercially available, stain-resistant nylon carpet samples were used for this experiment. These were:

Carpet #1—nylon 66 staple, 36 oz/sq.yd, light beige shade, sulfonated phenol formaldehyde condensate applied by carpet mill as a stain-blocker.

Carpet #2—nylon 66 staple, 35 oz/sq.yd, beige shade, stain-blocker (type not known) applied by fiber producer.

Carpet #3—nylon 6 bulked continuous filament, 35 oz/sq.yd, light beige shade, stain-blocker (type not known) applied by carpet mill.

Carpet #4—nylon 6 staple, 35 oz/sq.yd, light beige shade, stain-blocker (type not known) applied by carpet mill.

Treatment A

Samples of each of the above carpets were steam cleaned, dried, and stained with "Kool-Aid" using Stain Test 2 as described above. After 24 hours each was stain-rated.

Treatment B

A second sample of each of the above carpets was steam cleaned, and, while the fibers were still in moist condition, was topically oversprayed with an antimicrobial known as "Microban" X-580 manufactured by Microban Germicide Co., P. O. Box 777, Braddock, PA 15104. "Microban" X-580 is described as a broad spectrum disinfectant useful against most bacteria, insects, fungus and odors caused by bacteria and germs. (The composition of "Microban" X-580 is said to be isopropyl alcohol 25.0%, para-di-iso-butyl-phenoxyethoxyethyl-dimethylbenzyl-ammonium-o-phenylphenate bromine complex 0.85%, n-octyl-bi-cycloheptane-dicarboxyimide 0.4%, piperonyl butoxide 0.2%, pyrethrins 0.1%, and inert ingredients 73,448%). The same model two gallon (7.5 liter) capacity pressurized sprayer used in Example III was used for this overspray application. The antimicrobial agent was applied in accordance with the manufacturer's recommended procedures, and the sprayed mixture was then worked into the pile fiber using a pile brush. The treated samples were allowed to air dry and then stain-tested as per Stain Test 2.

Treatment C

A third sample of each of the above carpets was steam cleaned and sprayed with the antimicrobial "Microban" X-580 as per Treatment B. Fifteen minutes following this treatment, while the carpets were still in a moist condition, the samples were oversprayed with a mixture containing "Intratex" 30, "Teflon" MF and water in 2.24:1:30 (by volume) proportion: "Intratex" 30 is a commercial sulfonated phenol formaldehyde condensate sold by Crompton & Knowles Corporation. "Teflon" MF is an anionic fluorochemical manufactured by E. I. du Pont de Nemours and Company. The estimated amount of active stain-resist was 0.4% owf. The oversprayed mixture was then worked into the pile fiber and air-dried samples were stain-tested, as per Stain Test 2.

The stain results for the above treatments were as follows:

| | STAIN-RATING | | |
|---|---|---|---|
| | Treatment A | Treatment B | Treatment C |
| Carpet #1 | 4–5 | 3–2 | 5 |
| Carpet #2 | 4 | 3 | 5 |
| Carpet #3 | 3 | 1–2 | 3–4 |
| Carpet #4 | 4 | 1 | 4 |

EXAMPLE XII

Treatment A

A commercially-available, bulked continuous filament 36 oz./sq.yd nylon carpet, (light beige shade) was tested using Stain Test 2 and found to have a stain rating of 5.

Treatment B

A second sample of the same carpet was cleaned with Sear's detergent ("Cleanmore" Carpet Cleaner #1) in accordance with the manufacturer's recommended procedures, and, while still in a moist condition, the carpet was oversprayed with "Microban" X-580 using a "Preval" spray unit (Precision Valve Corp., Yonkers, NY 10702). The antimicrobial agent was worked-in using a hand-held pile brush, and the sample was allowed to air dry. The dried sample was then stain-tested as per Stain Test 2 and found to have a stain-rating of 3–4, showing a deterioration in stain performance following treatment with an antimicrobial.

Treatment C

A third sample of the same carpet was steam-cleaned and oversprayed with "Microban" X-580 antimicrobial as per Treatment B of this Example, except that the sprayed sample was allowed to air-dry for 3 hours and was then washed with cold tap water and again air-dried. The sample was then stained per Stain Test 2 and found to have a stain rating of 3–4 indicating that no difference in stain performance is obtained merely by washing the sample with tap water.

Treatment D

A fourth sample of the same carpet was steam-cleaned and oversprayed with "Microban" X-580 antimicrobial as per Treatment B of this Example. Fifteen minutes following this treatment, while the fibers were still in a moist condition, the sample was oversprayed with the same mixture as described in Treatment C of Example XI. The dried sample was then tested as per Stain Test 2 and found to have a stain-rating of 5.

EXAMPLE XIII

Two commercially-available, bulked continuous filament nylon carpet samples were used for this experiment: a 42 oz/sq.yd carpet and a 37 oz/sq.yd carpet, both in light beige shade. These carpets were stain tested using Stain Test 2 and found to have a stain rating of 5. Two deodorizing agents were selected to demonstrate the effect on stain performance of these carpets: Agent #1, a scented disinfectant containing the active ingredients o-phenylphenol 2.8% and benzyl-o-chlorophenol 2.7% and Agent #2, a lemon scented deodorizer containing the cationic disinfectant alkyl dimethyl benzyl ammonium chloride with a dye and fragrance.

Treatment A

Diluted aqueous solutions (2 fluid oz/gallon) of each of the above deodorizers were prepared, and 20 ccs of each of these diluted solutions were poured on different samples of each of the carpets using the sam technique as described in Stain Test 2. After 15 minutes, the solution was thoroughly blotted and wet-vacuumed so the four carpet samples were almost dry. The samples were then stained on the same spot with "Kool-Aid" as per Stain Test 2. Both carpets (all four samples) showed heavy staining with a stain rating of 2.

Treatment B

Solution A—a 10% aqueous solution was prepared from an 80/20 mixture of hydrolyzed styrene/maleic anhydride polymer and acetylated Mesitol NBS, as described in Example 1 of copending application Ser. No. 07/136,033.

Solution B—1 part of an anionic fluorochemical was diluted with 15 parts of water.

Solution C—50/50 volumetric mixture of solution A and B.

Solution D—15 ccs of diluted Agent #1 (2 fluid oz/-gallon of water) and 5 ccs of solution C.

Solution E—15 ccs of diluted Agent #2 (2 fluid oz/-gallon of water) and 5 ccs of solution C.

Solutions D and E were separately applied to samples of both carpets using the same technique as described in Treatment A of this Example and stain-tested using Stain Test 2. Both carpets (all four samples) had the fragrance of the deodorizer and showed no visible staining with a stain-rating of 5. Thus this Example demonstrates that an improvement in stain-resistance can be effectively achieved by combining a cationic deodorizers containing germicidal disinfectants with a stain (and soil-) resist agent, although as previously described a soil-resist chemical is not necessary to obtain stain improvement.

EXAMPLES XIV-XVI

The following are applicable to these examples:

*Bacterial Culturing and Enumeration Method*—Bacterial inocula were prepared by transferring 2.0 ml of an overnight broth culture to a 300 ml nephyloculture flask (Bellco Glass Inc., Vineland, N.J.) containing 100 ml of Tryptic Soy Broth (TSB) (Remel, Lexena, KS). This flask was incubated at 37° C with shaking (ca. 200 rpm). Growth of the culture was determined during incubation using a Klett-Summerson photoelectric colorimeter (Klett Mfg. Co., NY, NY). When the culture reached late log phase, the culture was diluted to the desired concentration in sterile phosphate buffer dilution water (PBDW)(AOAC Methods, sec. 4.023 (f)). Enumeration of bacterial population entailed removing a 1.2 ml aliquot from the material to be enumerated, spread plating 0.1 ml onto two Trypticase Soy Agar (TSA) plates, serial diluting the remaining 1.0 ml, and spread plating the dilutions in duplicate on TSA plates. These plates were incubated at 37° C. for 18–24 hours. Plates having between 30 and 300 colonies were counted and the bacterial concentration determined from the mean of the plate counts. If none of the plates contained at least 30 colonies, the bacterial concentration was determined from the mean of the plates having colonies.

Carpet Preparation—BCF (bulked continuous filament) nylon 6,6 1110-68 yarns, i.e. 1110 denier and 68 filaments, of trilobal crossection were produced by a conventional process. Pairs of these yarns were plied and twisted to produce yarns having a balanced twist of 4.5 tpi (turns per inch ). The resulting yarns were then heat-set at 270° F. in a Superba heat-setting machine. A cut pile tufted carpet was constructed from the heat set yarns, and a conventional polypropylene primary backing was applied to produce a carpet having the following specifications:—42 oz./sq.yd; $\frac{1}{2}$ inch pile height; 1/10 gauge; 31 stitches per 3 inches. This carpet was dyed to a light beige shade using a conventional batch dye process, dye auxillaries and the following dye formula, based on weight of carpet, 0.011% C.I.Acid Yellow 219, 0.0094% C.I.Acid Red 361, 0.008% C.I.Acid Blue 277 at a pH of 6.5. After dyeing, the carpet was treated in a bath containing 2.5% o.w.f. of the acetylated Mesitol NBS solution as referred to in the Application S.N. 943,335, at 170° F for 20 min. at pH 2.5, using approximately a 20:1 liquor ratio. The carpet was then rinsed, topically treated with a commercial fluorochemical (equivalent to cationic version of "Teflon" Toughcoat, available from E.I. du Pont de Nemours and Co., Wilmington, De.,) and dried, latexed, cured and tip sheared.

EXAMPLE XIV

A 7 ft × 12 ft section of the test carpet was delineated into quadrants measuring approximately 31 in × 26 in (806 sq. in. = 5.6 sq. ft). In the center of three of these quadrants, 100 ml of canine (beagle) urine was applied by pouring the urine through a funnel having a small orifice so as to mimic the natural contamination process. The carpet was then turned over and the urine containing area on the carpet backing was outlined with a permanent marker for further reference. The carpet was then turned pile side-up and allowed to age for 2.5 days at room temperature. Prior to any further treatment, a 2 × 2 inch piece was cut from within the outlined urine contamination area of each quadrant. The carpet samples were placed into sterile 250 ml Erlenmyer flasks containing 100 ml of sterile PBDW and shaken for 5 minutes. Plate counts were performed as previously described. The quadrants were then treated as follows:

Quadrant 1: Treated for 15 minutes with 210 ml of a composition containing 1.56 ml "UCARSAN" 4128, 20.0 ml of a stain-resist solution, diluted to 1.0 liter with distilled water "UCARSAN" 4128 (Union Carbide Corporation, Danbury, CT) is a solution containing 12.8% glutaraldehyde, <0.03% methanol, and approximately 87.2% of an aqueous surfactant solution. The stain-resist solution was composed of 46.51% water, 5.81% of a 50% citric acid solution, 5.81% of a sulfonated phenol-formaldehyde condensation product, 29.07% of a hydrolyzed styrene/maleic anhydride polymer, and 12.80% "Teflon" MF. Treatment was accomplished using a hand-held spray bottle. This application rate is equivalent to one gallon per 100 sq. ft.

Quadrant 2: Treatment with 210 ml of distilled water as described above.

Quadrant 3; Was not treated after addition of the canine urine. Used as a control to determine the background microbial population due to the urine.

Quadrant 4: Did not receive any canine urine or treatment. Used as a control to determine the background microbial population of uncontaminated carpet.

After treatment each quadrant was sampled by removing another 2×2 inch section and the microbial population determined as described above.

TABLE 1

| Antimicrobial Activity Associated with Treatment of Carpets Contaminated with Canine Urine | | | | |
|---|---|---|---|---|
| | Microbial Population (colony forming units/4 in$^2$) | | Population Reduction | |
| Quadrant | Initial | Post Treatment | Percent | Log |
| 1 | $4.5 \times 10^5$ | $1.0 \times 10^3$ | 99.7[a] | 2.47 |
| 2 | $2.5 \times 10^5$ | $6.0 \times 10^7$ | NA | −2.31[b] |
| 3 | $1.8 \times 10^5$ | $7.4 \times 10^6$ | NA | −1.40 |
| 4 | $1.0 \times 10^3$ | $1.3 \times 10^3$ | NA | −0.11[c] |

[a]Reduction was calculated using the mean of the initial population for quadrants 1-3.
[b]Negative values represent an increase in the microbial population.
[c]Reduction of the population was calculated from the initial population determined for quadrant 4.

It is evident that the microbial population associated with carpet contaminated with canine urine is significantly reduced (>90%) by treatment of the carpet using the product and process described.

EXAMPLE XV

Antimicrobial Effectiveness of Composition *In Vitro*

*In Vitro* efficacy was determined against *Staphylococcus aureus* ATCC 6538, *Enterobacter aerogenes* ATCC 13048, *Pseudomonas aeruginosa* ATCC 15442 cultures grown as described above.

Each bacterial culture was diluted to a concentration between $1.0 \times 10^5$ and $1.0 \times 10^6$ colony forming units per milliliter (cfu/ml) in sterile distilled water using the Klett colorimeter. Actual concentrations were determined by serial dilution and spread plating as described above. 5.0 ml of dilute culture was added to sterile test tubes. 120 microliters of a concentrated stain-resist composition (comprised of 116.2 ml of the same stain-resist solution described in Example XIV, 18.15 ml UCARSAN™ 4128, 131.8 ml distilled water) was added to each tube to give a final glutaradehyde concentration of 200 ppm (active). Aliquots were removed from each test tube (after 1, 3, 6, and 10 minutes), serial diluted, and spread plated as described in above.

TABLE 2

| Effectiveness of Antimicrobial Agent In Vitro CFU/ML AFTER CONTACT TIME (MIN) | | | | | | |
|---|---|---|---|---|---|---|
| | Agent | Minutes of Contact Time | | | | |
| Organism | Present | 0 | 1 | 3 | 6 | 10 |
| *S. aureus* | no | $9.50 \times 10^5$ | $1.33 \times 10^6$ | $1.31 \times 10^6$ | $1.46 \times 10^6$ | $1.19 \times 10^6$ |
| | yes | $9.50 \times 10^5$ | $4.00 \times 10^1$ | $2.00 \times 10^1$ | <10 | <10 |
| *E. aerogenes* | no | $4.95 \times 10^5$ | $4.70 \times 10^5$ | $5.65 \times 10^5$ | $5.10 \times 10^5$ | $4.35 \times 10^5$ |
| | yes | $4.95 \times 10^5$ | $4.75 \times 10^5$ | $1.72 \times 10^5$ | $8.85 \times 10^2$ | $3.00 \times 10^1$ |
| *P. aeuruginosa* | no | $1.05 \times 10^5$ | $1.72 \times 10^5$ | $2.42 \times 10^5$ | $3.07 \times 10^5$ | $3.17 \times 10^5$ |
| | yes | $1.05 \times 10^5$ | $1.84 \times 10^5$ | $1.45 \times 10^5$ | $9.20 \times 10^3$ | $1.01 \times 10^3$ |

The composition containing both the stain-resist solution and glutaraldehyde (200 ppm active) reduced the populations of *S. aureus, E. aerogenes*, and *P. aeruginosa* by at least 90% after 6 minutes indicating the antimicrobial agent remains efficacious in the presence of the stain-blocker.

EXAMPLE XVI

A portion of the uncontaminated carpet from Quadrant 4 of Example XIV was cleaned with 4 passes of a portable hot wet extraction machine, Century 400 model, (available from Accomodation Sanitory Supply Co., Philadelphia, Pa) using 2 oz. per gallon solution of the Spartan X-traction II detergent solution (also available from Accomodation Sanitory Supply Co.). The carpet was allowed to dry in air and was then stain-tested as per Stain Test 2. The Stain rating was not slight-staining i.e., a rating of 4.

A second sample of this uncontaminated carpet was first treated with canine urine and then with the same composition as was used to treat Quadrant 1 of Example XIV. The sprayed-on mixture was then worked into the pile fiber using a pile brush. After allowing the composition to remain in contact with the carpet for about 15–20 minutes, the carpet was cleaned using the same portable hot wet extraction unit and the detergent solution in the same manner as described above. The cleaned carpet was allowed to dry in air and then stain tested as per Stain Test 2. The carpet showed no visible stain (stain rating of 5).

We claim:

1. An aqueous stain-resist composition having antimicrobial activity comprised of an effective amount of both a stain-blocker and an antimicrobial agent, the stain-blocker being selected from the group consisting of a sulfonated phenol-formaldehyde condensate polymer, a sulfonated naphthol-formaldehyde condensate polymer, a hydrolyzed vinyl aromatic maleic anhydride polymer and any combination thereof, the antimicrobial agent being gluteraldehyde.

2. The composition of claim 1 further comprising a fluorochemical.

* * * * *